United States Patent
Kim

(12) 
(10) Patent No.: US 10,293,067 B2
(45) Date of Patent: May 21, 2019

(54) TWO-SIDED, SURFACE LIGHT SOURCE DEVICE USING LED

(71) Applicant: SEOUL VIOSYS CO., LTD., Gyeonggi-do (KR)

(72) Inventor: Jae Jo Kim, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 0 days.

(21) Appl. No.: 15/531,414

(22) PCT Filed: Nov. 4, 2015

(86) PCT No.: PCT/KR2015/011809
§ 371 (c)(1),
(2) Date: May 26, 2017

(87) PCT Pub. No.: WO2016/085144
PCT Pub. Date: Jun. 2, 2016

(65) Prior Publication Data
US 2017/0319726 A1     Nov. 9, 2017

(30) Foreign Application Priority Data
Nov. 28, 2014   (KR) .......................... 10-2014-0168872

(51) Int. Cl.
*A61L 2/10*     (2006.01)
*F21V 8/00*    (2006.01)

(52) U.S. Cl.
CPC .............. *A61L 2/10* (2013.01); *G02B 6/0021* (2013.01); *G02B 6/0036* (2013.01);
(Continued)

(58) Field of Classification Search
CPC ..... A61L 2/10; A61L 2202/11; G02B 6/0076; G02B 6/0061; G02B 6/0036;
(Continued)

(56) References Cited

U.S. PATENT DOCUMENTS

2008/0219025 A1   9/2008   Spitzer et al.
2008/0266902 A1*  10/2008  Zheng .................. G02B 6/0041
                                                                362/618
(Continued)

FOREIGN PATENT DOCUMENTS

CN      1530708 A      9/2004
CN      1627149 A      6/2005
(Continued)

OTHER PUBLICATIONS

International Search Report and Written Opinion for PCT/KR2015/011809, filed Nov. 4, 2015, Applicant: Seoul Viosys Co., Ltd., dated Feb. 24, 2016, ISA/KR, 10 pages.
(Continued)

*Primary Examiner* — Michael Maskell
(74) *Attorney, Agent, or Firm* — Perkins Coie LLP

(57) ABSTRACT

Disclosed herein is a light source device using light-emitting diodes (LEDs). Specifically, a two-sided, surface light source device is implemented with point light sources such as LEDs in a simple configuration, such that even surface light is emitted. The two-sided, surface light source device includes: a substrate on which light-emitting diodes (LEDs) are disposed as a light source; and a two-sided diffusion unit having a plate-like shape with a front side face, a back side face, and a light-receiving face that is perpendicular to the front side face and the back side face and faces the substrate. Light emitted from the light source is diffused in the diffusion unit and exits through the front side face and the back side face.

18 Claims, 9 Drawing Sheets

(52) U.S. Cl.
CPC ......... *G02B 6/0041* (2013.01); *G02B 6/0046* (2013.01); *G02B 6/0061* (2013.01); *G02B 6/0063* (2013.01); *G02B 6/0068* (2013.01); *G02B 6/0076* (2013.01); *A61L 2202/11* (2013.01)

(58) Field of Classification Search
CPC .. G02B 6/0063; G02B 6/0046; G02B 6/0041; G02B 6/0021; G02B 6/0068
USPC ...................................... 349/62, 64
See application file for complete search history.

(56) References Cited

U.S. PATENT DOCUMENTS

| | | | |
|---|---|---|---|
| 2009/0207339 A1* | 8/2009 | Ajichi | ................ G02B 5/0242 349/64 |
| 2010/0141868 A1* | 6/2010 | St. Hilaire | ........... G02B 6/0036 349/62 |
| 2011/0273902 A1 | 11/2011 | Chang et al. | |
| 2012/0169967 A1* | 7/2012 | Han | ..................... G02F 1/1333 349/62 |

FOREIGN PATENT DOCUMENTS

| | | | |
|---|---|---|---|
| JP | 2001101916 A | | 4/2001 |
| KR | 102009016100 A | | 2/2009 |
| KR | 1020110081569 A | | 7/2011 |
| KR | 20120052627 A | * | 5/2012 |
| KR | 1020120052627 A | | 5/2012 |

OTHER PUBLICATIONS

Search Report in European Patent Application No. EP15864200, dated May 30, 2018.
Chinese Official Action from related Chinese Patent Application dated Dec. 13, 2018 (2 pages).

* cited by examiner

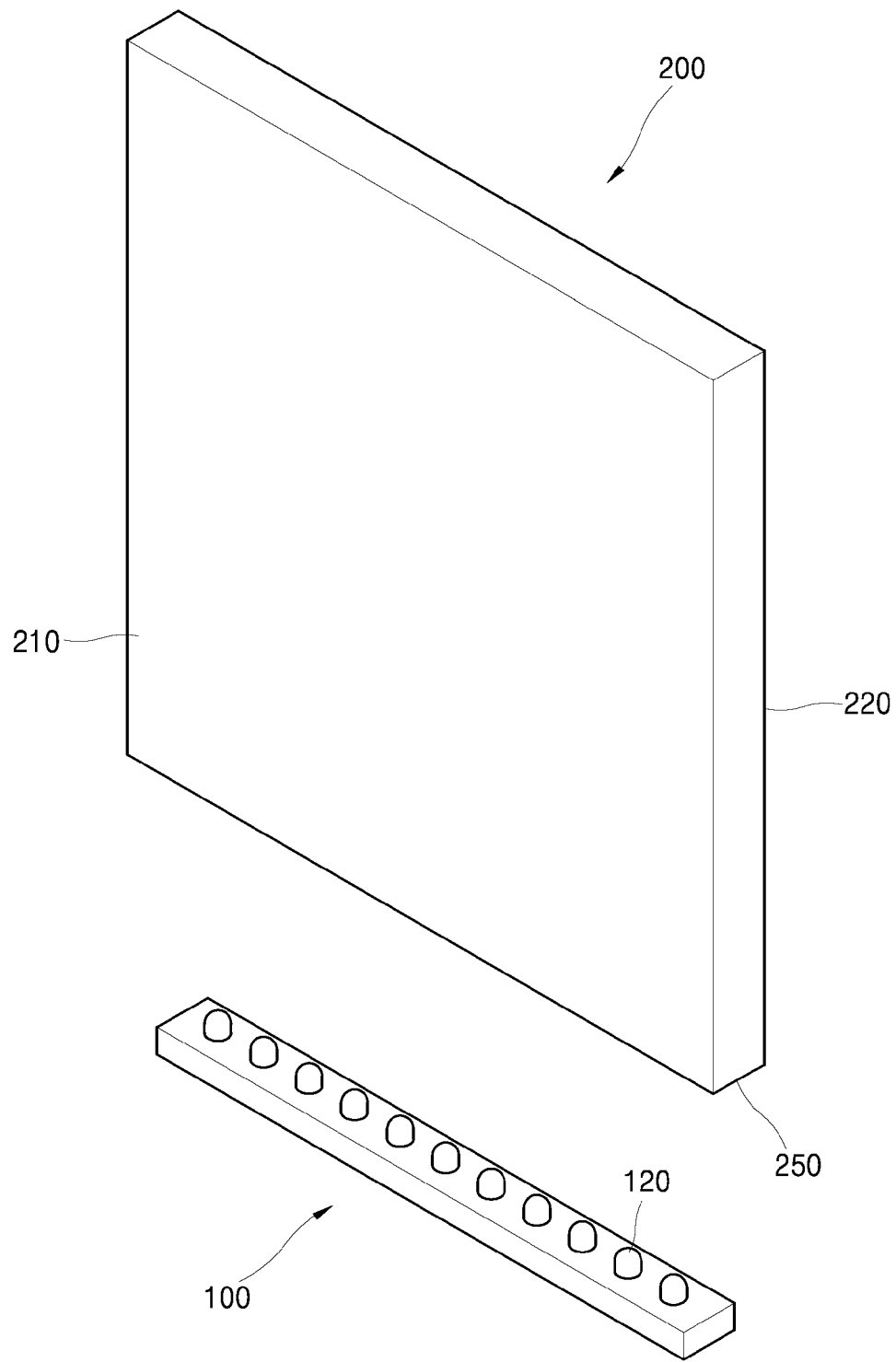
[Fig. 1]

[Fig. 2]
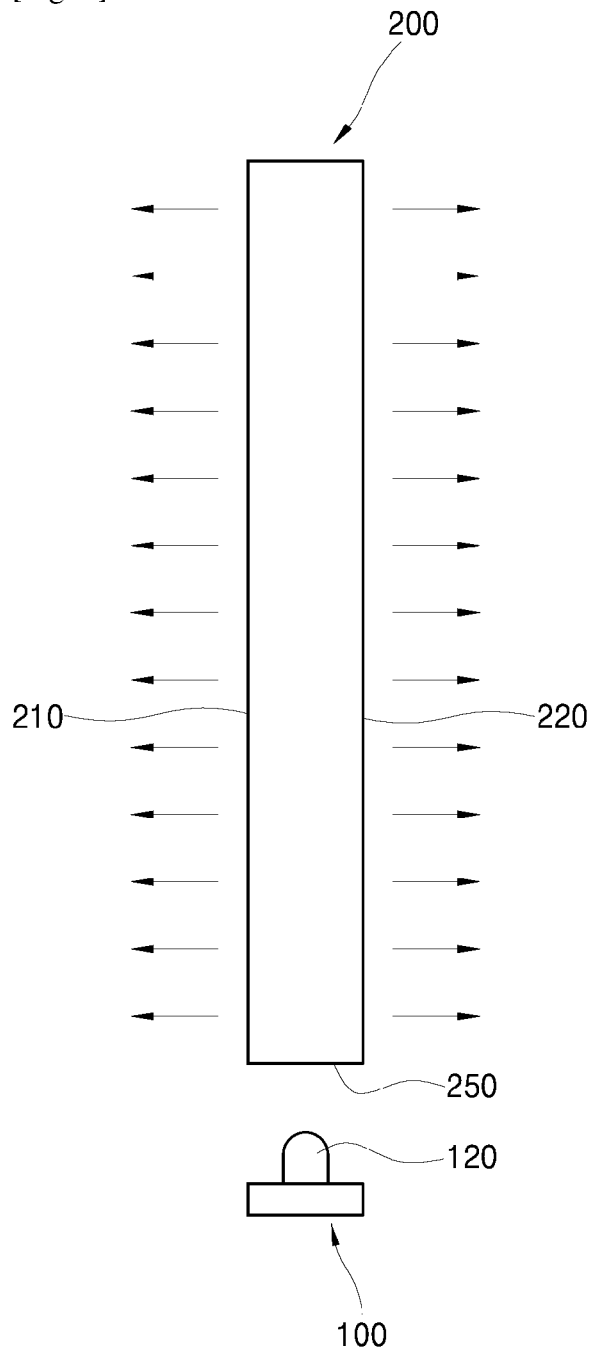

[Fig. 3]
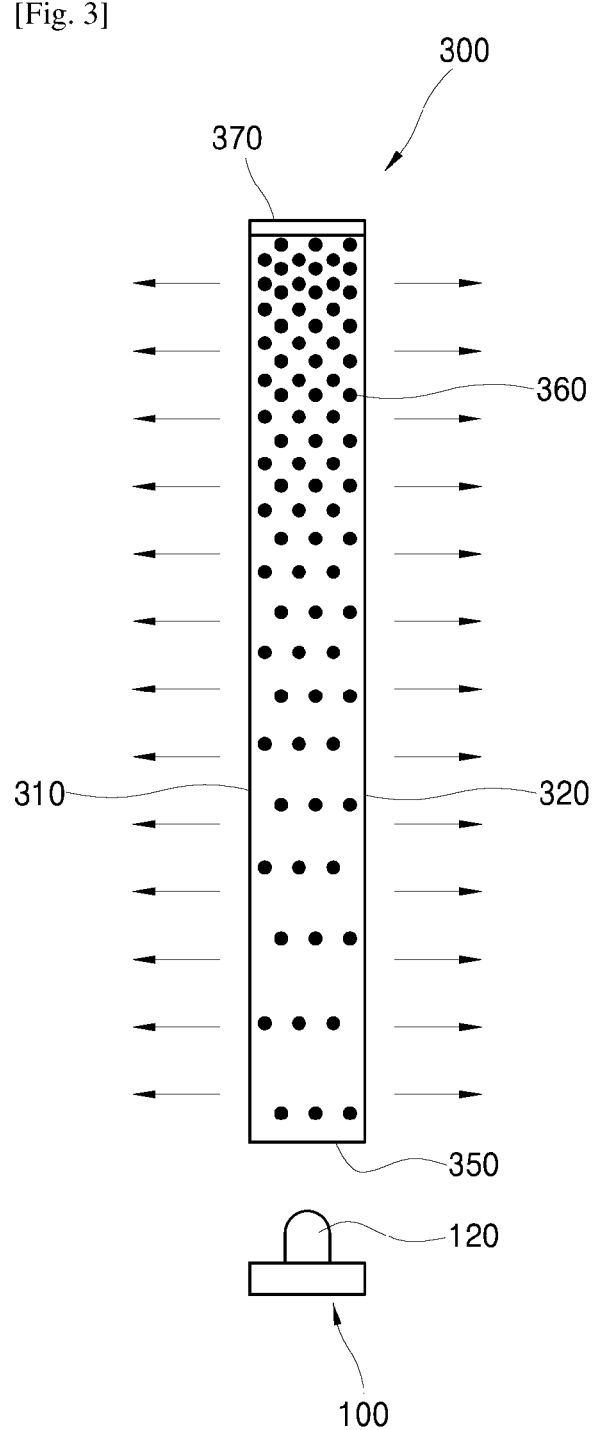

[Fig. 4]
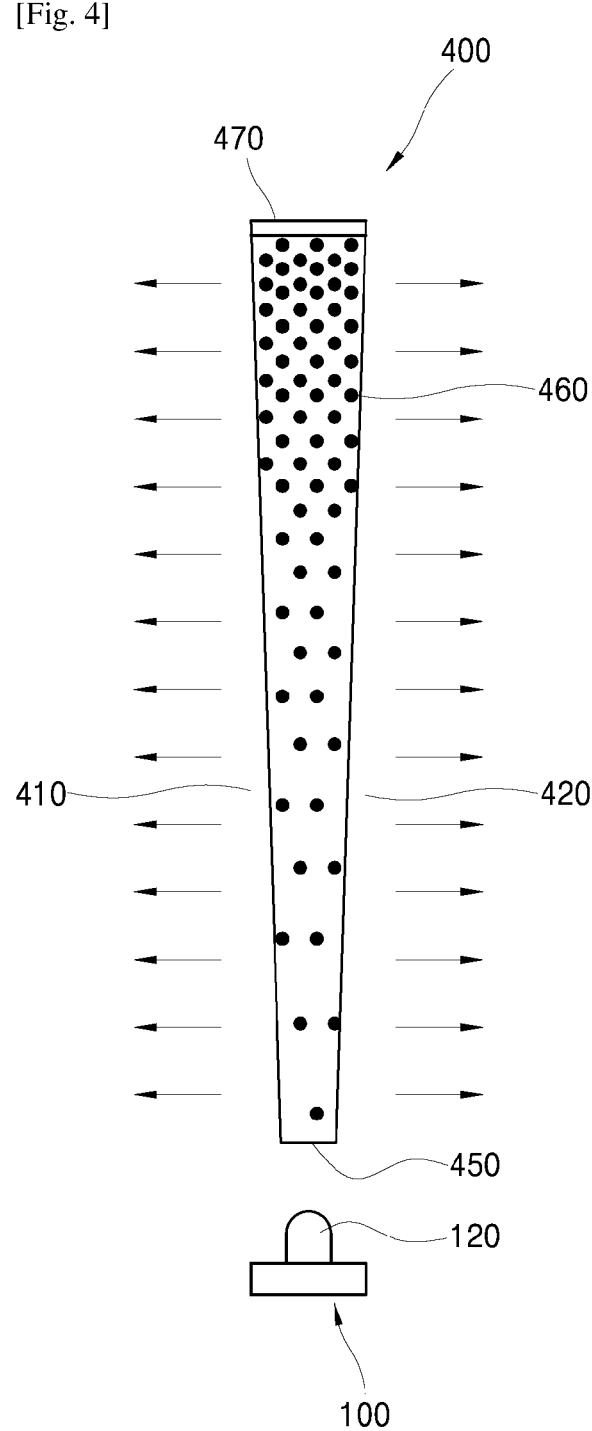

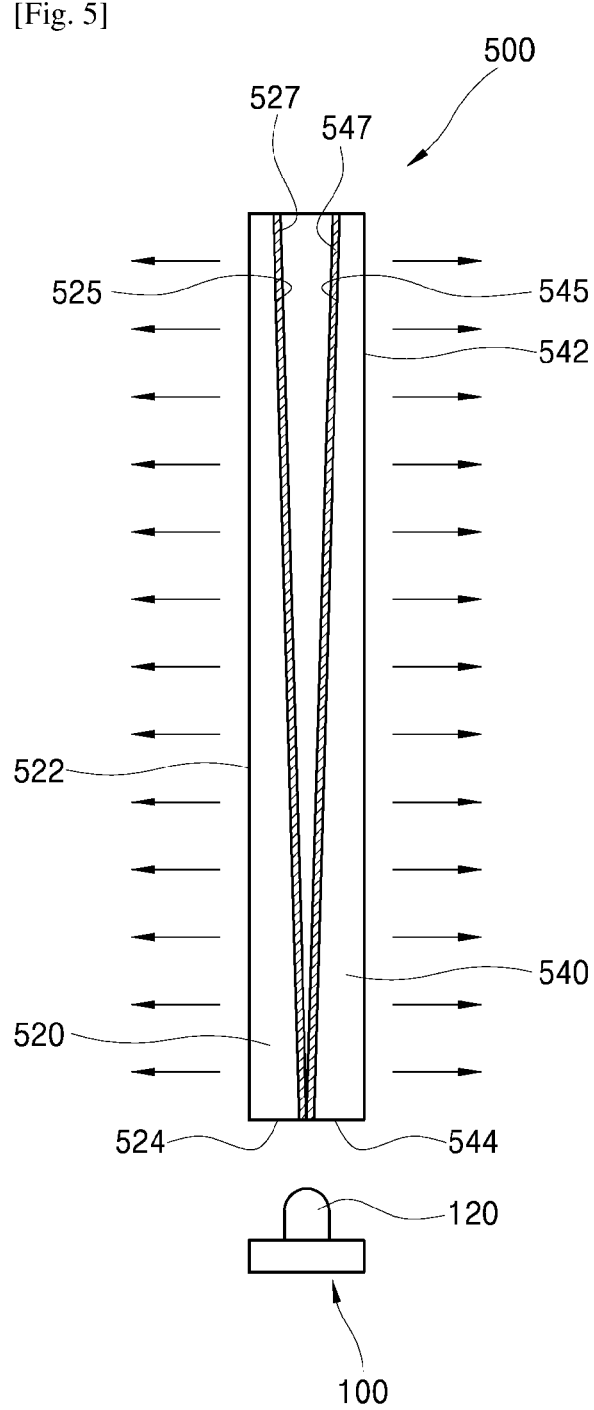
[Fig. 5]

[Fig. 6]
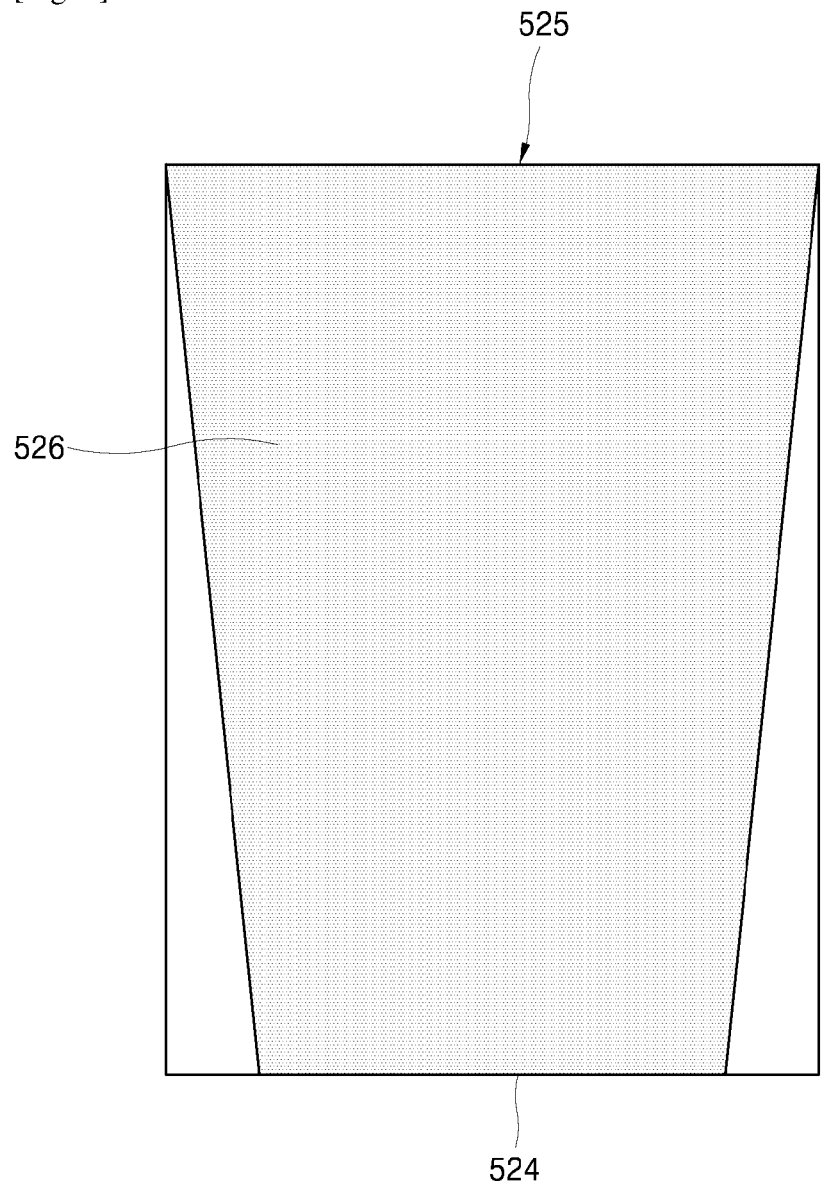

[Fig. 7]
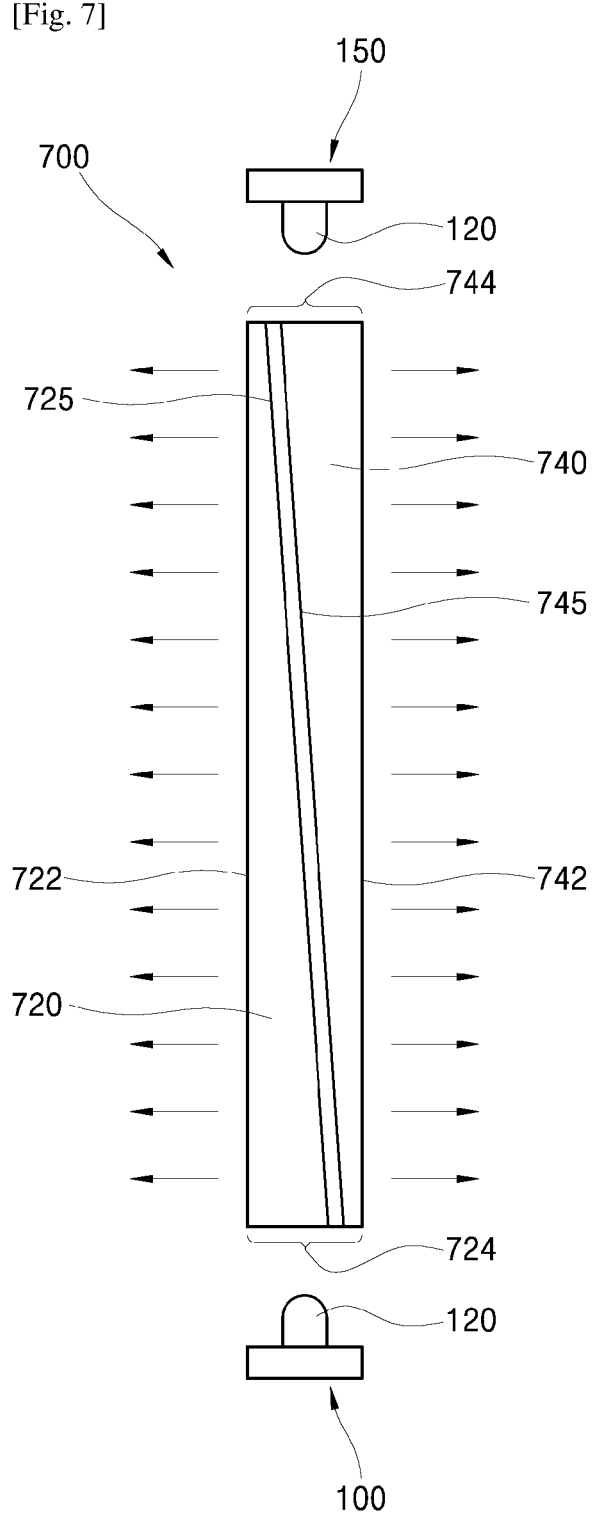

[Fig. 8]
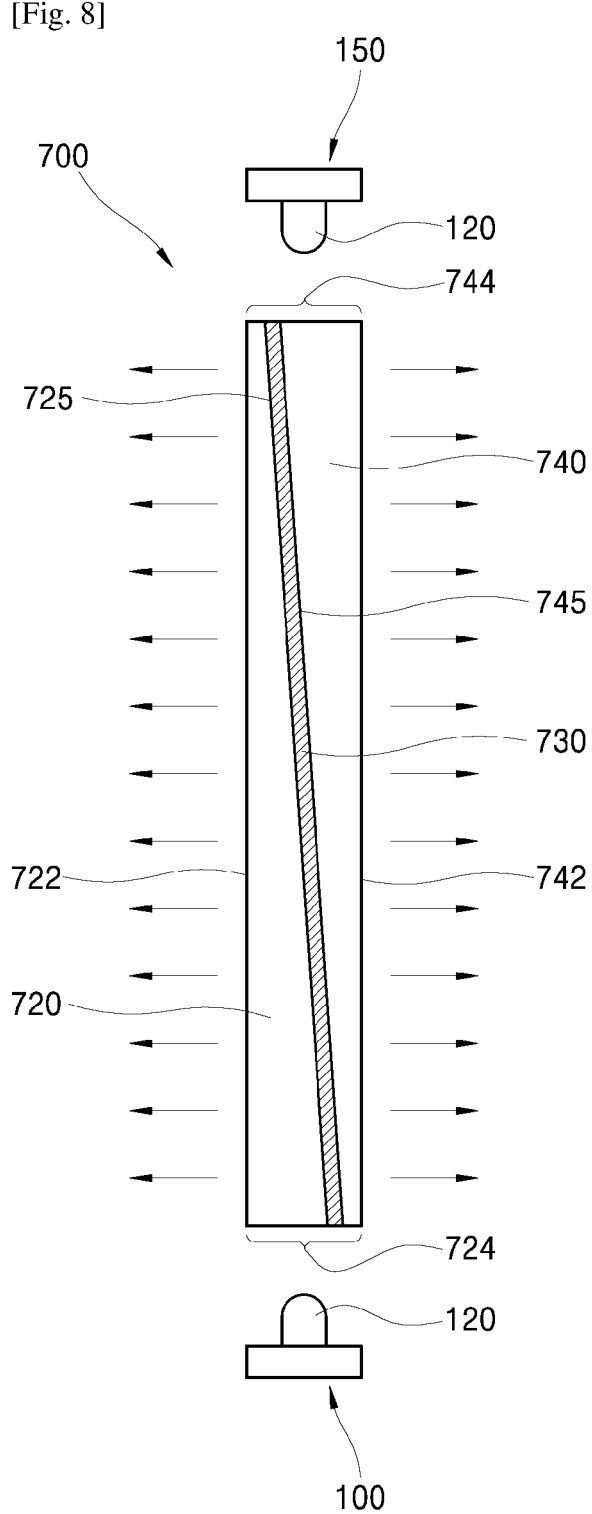

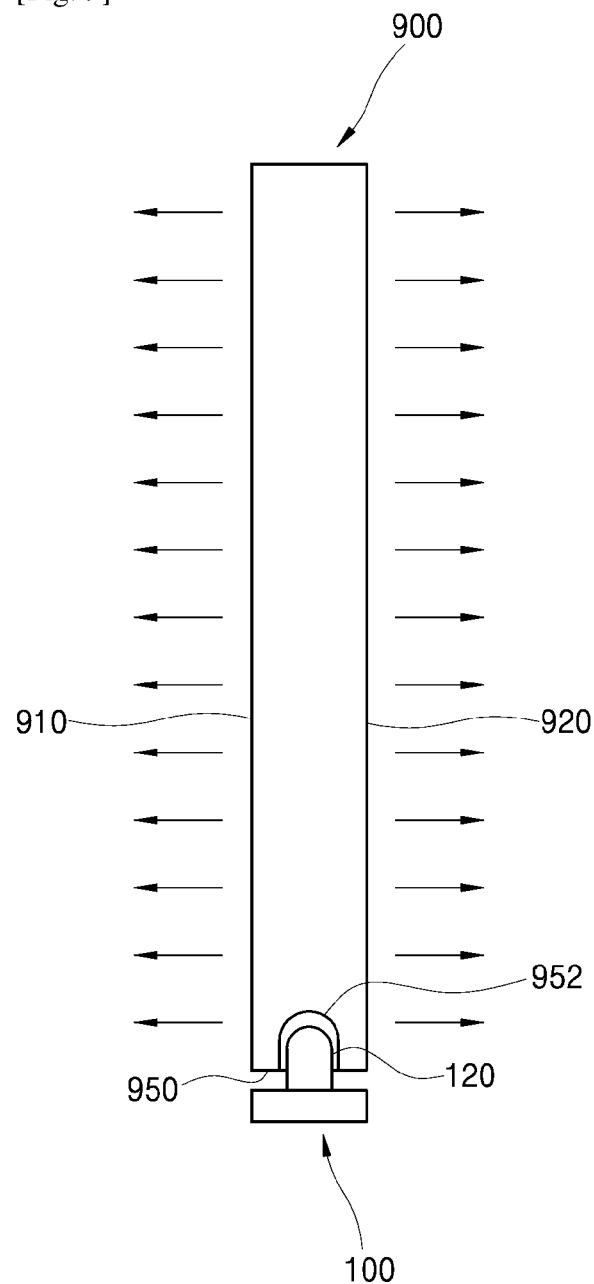
[Fig. 9]

TWO-SIDED, SURFACE LIGHT SOURCE DEVICE USING LED

CROSS REFERENCE TO RELATED APPLICATION

This patent document is a 35 U.S.C. § 371 National Stage application of PCT Application No. PCT/KR2015/011809, filed on Nov. 4, 2015, which further claims the benefits and priorities of prior Korean Patent Application No. 10-2014-0168872, filed on Nov. 28, 2014. The entire disclosures of the above applications are incorporated by reference in their entirety as part of this document.

TECHNICAL FIELD

The present disclosure relates to a light source device using ultraviolet light-emitting diodes (UV LEDs), and more particularly to a two-sided, surface light device having a simple configuration for implementing a surface light source with point light sources such as UV LEDs.

BACKGROUND ART

UV light sources have a variety of applications including: medical uses such as disinfection and sterilization; analytic uses utilizing change in irradiated UV light; industrial uses such as UV curing; cosmetic uses such as UV tanning; insect trap; counterfeit currency check, etc.

Traditionally, UV light source lamps used as such UV light sources include mercury lamps, excimer lamps, deuterium lamps, etc. Unfortunately, such existing lamps have problems in that they have high power consumption, generate much heat, have a short lifespan, and result in environmental contamination due to toxic gases filling therein.

In light of the above-described problems, UV LEDs are attracting attention as a solution for such problems. UV LEDs have advantages in that they have low power consumption and do not result in environmental contamination. However, manufacturing cost for an LED package emitting light in the UV range is much higher than that of an LED package emitting light in the visible range. In addition, UV light has unique characteristics, and thus it is difficult to develop various applications using an LED package.

For example, in order to manufacture lamp products using UV LEDs, the following issues have to be considered. One of the issues relates to a diffusion unit. In order to manufacture be a lamp using UV LED chips, a diffusion unit is required that is made of an appropriate transparent material such that it covers and protect the UV LED chips and transmits UV light. If the diffusion unit is made of quartz (glass), although it can transmit UV light of a single wavelength, it has to be handled with care since it is easily broken. In addition, such a diffusion unit has poor formability and low dissipation performance.

In view of this, a polymer that has better formability, is easier to handle and has better durability than quartz may be contemplated. However, a polymer exhibits low light transmittance since light having a wavelength of 400 nm or less (ultraviolet wavelength range) is absorbed by electron cloud which exists around a nuclear core and having a resonant frequency corresponding to that of UV. In addition, a diffusion unit made of a polymer itself may deteriorate by UV light. Thus, a polymer is not an appropriate material for a diffusion unit. In this regard, it is known that pure poly methyl methacrylate (PMMA) consists primarily of carbon and hydrogen and thus rarely has electron cloud, such that it exhibits high UV transmittance.

Another of the issues relates to the light distribution characteristics of LEDs. A pure PMMA, mentioned above, is a transparent material, and thus light sources and circuit parts disposed in a diffusion unit made of a pure PMMA is visible by observers, harming the aesthetic appearance. In addition, the center portion of the light source looks brighter due to the light distribution characteristics of LEDs, and thus it is difficult to achieve even illumination. If LEDs are disposed more densely in order to achieve even illumination, the cost of a UV LED light source device is greatly increased due to high price of a UV LED package.

In addition, when a UV LED light source device is employed as a light source of an insect trap lamp, it cannot attract insects effectively due to a hot spot. Further, for commercial uses such as UV curing or cosmetic uses such as tanning, a surface light source providing even UV illumination is preferred to point light sources. Accordingly, it is increasingly required to implement a UV LED lamp as a surface light source.

DISCLOSURE OF INVENTION

Technical Problem

An aspect of the present invention is to provide an LED surface light source device that emits light through two side faces thereof using point light sources such as LEDs.

Solution to Problem

In accordance with one aspect of the present disclosure, a two-sided, surface light source device includes: a substrate on which light-emitting diodes (LEDs) are disposed as a light source; and a two-sided diffusion unit having a plate-like shape with a front side face, a back side face, and a light-receiving face that is perpendicular to the front side face and the back side face and faces the substrate. Light emitted from the light source is diffused in the diffusion unit and exits through the front side face and the back side face.

The two-sided diffusion unit may include diffusion particles. The density of the diffusion particles may increase away from the light-receiving face.

The two-sided diffusion unit may have a wedge-like cross section that widens away from the light-receiving face.

The two-sided diffusion unit may include a first light guide plate diffusing light received through the light-receiving face toward the front side face, and a second light guide plate diffusing the light received through the light-receiving face toward the back side face.

The two-sided diffusion unit may further include a reflective plate on a side face opposed to the light-receiving face.

The first and second light guide plates may have inclined faces opposed to light-exiting faces, respectively, and a diffusion pattern may be formed between the inclined faces.

The area of the diffusion pattern may increase away from the light-receiving face.

A reflective layer may be formed in the inclined face of each of the first and second light guide plates.

The two-sided diffusion unit may include a light source groove in which the LEDs are accommodated.

Another aspect of the present disclosure is to provide a two-sided, surface light source device using LEDs, including: a first substrate on which LEDs are disposed as a light source; a second substrate on which LEDs are disposed as a light source; and a two-sided diffusion unit having a plate-like shape, a side face of the two-sided diffusion unit being a first light-receiving face facing the first substrate and the other side face of the two-sided diffusion unit being a second light-receiving face facing the second substrate. Lights emitted from the light sources are diffused in the diffusion unit and exit through a front side face and a back side face.

The two-sided diffusion unit may include a first light guide plate diffusing light received through the first light-receiving face toward the front side face, and a second light guide plate diffusing the light received through the second light-receiving face toward the back side face.

The first and second light guide plates may have a wedge-like shape, and the two-sided diffusion unit may be formed by stacking the first light guide plate on the second light guide plate with their inclined faces face each other.

The first light guide plate and the second light guide plate may have reflective layers on their inclined faces, respectively, or a two-sided reflective plate may be disposed between the inclined faces.

Each of the first and second light guide plates may have a light source groove in which the LEDs are accommodated.

Advantageous Effects of Invention

According to exemplary embodiments of the present disclosure, it is possible to form a large and even light illumination area using a small number of LEDs, by directing light emitted from point light sources such as LEDs to exit through two side faces of a diffusion unit.

BRIEF DESCRIPTION OF DRAWINGS

FIG. 1 is a perspective view conceptually illustrating a basic structure of a two-sided, surface light source device using LEDs according to an exemplary embodiment of the present disclosure;

FIG. 2 is a side view conceptually illustrating the basic structure of the two-sided, surface light source device using LEDs according to the exemplary embodiment of the present disclosure;

FIG. 3 is a cross-sectional view of a two-sided, surface light source device according to a first exemplary embodiment of the present disclosure;

FIG. 4 is a cross-sectional view of a two-sided, surface light source device according to a second exemplary embodiment of the present disclosure;

FIG. 5 is a cross-sectional view of a two-sided, surface light source device according to a second exemplary embodiment of the present disclosure;

FIG. 6 is a plan view for illustrating a diffusion pattern by a diffusion unit according to the third exemplary embodiment of the present disclosure;

FIG. 7 is a cross-sectional view of a two-sided, surface light source device according to a fourth exemplary embodiment of the present disclosure;

FIG. 8 is a cross-sectional view of a two-sided, surface light source device according to a fifth exemplary embodiment of the present disclosure; and FIG. 9 is a cross-sectional view of a two-sided diffusion unit coupled with LEDs according to an exemplary embodiment of the present disclosure.

BEST MODE FOR CARRYING OUT THE INVENTION

Non-limiting exemplary embodiments of the present disclosure will now be described hereinafter. Such exemplary embodiments of the present disclosure may be embodied in many different forms and should not be construed as limited to the exemplary embodiments set forth herein. Rather, such embodiments are provided so that this application will be thorough and complete, and will fully convey the true scope of exemplary embodiments of the present disclosure to those skilled in the art.

Hereinafter, exemplary embodiments of the present disclosure will be described in detail with reference to the accompanying drawings.

FIG. 1 is a perspective view conceptually illustrating a basic structure of a two-sided, surface light source using LEDs according to an exemplary embodiment of the present disclosure. FIG. 2 is a side view conceptually illustrating the basic structure of the two-sided, surface light source using LEDs according to the exemplary embodiment of the present disclosure.

As shown in FIGS. 1 and 2, the surface light source device using LEDs according to the exemplary embodiment of the present disclosure includes a substrate 100 on which LEDs 120 are disposed as the light source, and a two-sided diffusion unit 200 having a plate-like shape with a front side face 210 and a back side face 220.

The two-sided diffusion unit 200 may be configured as a single plate or a plurality of plates stacked on one another.

The plate-like, two-sided diffusion unit 200 has six faces. Among the six faces, two largest faces opposed to each other are referred to as the front side face 210 and the back side face 220, respectively.

The two largest faces 210 and 220 are light-exiting faces through which UV light exits. A face 250 facing the substrate 100 on which the LEDs 120 are disposed is a light-receiving face. In other words, light incident on the light-receiving face 250 is evenly distributed in the two-sided diffusion unit 200, and then exits through the two faces 210 and 220.

If UV LEDs that emit ultraviolet ray are employed as the LEDs 120, the two-sided diffusion unit 200 may be made of a material that is transparent and has high transmittance of ultraviolet ray. For example, the two-sided diffusion unit 200 may be made of a polymethyl methacrylate (PMMA). Not all kinds of PMMA exhibit good transmittance of ultraviolet ray; it is found that a pure acryl containing smaller additives exhibits higher transmittance of ultraviolet ray, such as an acryl polymer containing methyl methacrylate (MMA) monomers of 85 weight % to 100 weight %.

Special acryl for increasing the transmittance of PMMA has poor formability compared to ordinary polymers, and thus it may be more difficult to produce than ordinary polymers. Notwithstanding such shortcomings, a PMMA is reasonable choice for the material of the two-sided diffusion unit, because it exhibits good transmittance and is not easily broken and thus easy to handle.

For example, quartz may also be employed for the material of the two-sided diffusion unit 200. Quartz is an ideal choice in that it exhibits high light transmittance over the entire range of wavelengths. However, quartz is difficult to produce and has to be handled with much care since it is extremely fragile. Accordingly, quartz is more difficult to apply than polymers.

FIG. 3 is a cross-sectional view of a two-sided, surface light source device according to a first exemplary embodiment of the present disclosure. FIG. 4 is a cross-sectional view of a two-sided, surface light source device according to a second exemplary embodiment of the present disclosure.

In the first exemplary embodiment shown in FIG. 3, a two-sided diffusion unit 300 is configured as a single plate, and the distribution of diffusion particles 360 therein are adjusted so that light exits evenly through two faces in the form of surface light.

The light emitted from the LEDs 120 passes through the two-sided diffusion unit 300 and are scattered by the diffusion particles, such that light exits through the two faces 310 and 320. Beads may be used for the diffusion particles 360.

In the two-sided diffusion unit 300 according to the first exemplary embodiment of the present disclosure, the density of the diffusion particles distributed in the two-sided diffusion unit 300 may increase away from the LEDs. In other words, the density of the diffusion particles 360 distributed in the two-sided diffusion unit 300 increases away from the light-receiving face 350. This distribution allows the light emitted from the LEDs 120 to exit evenly through the two faces as the light is reflected or refracted by the diffusion particles.

In addition, the surface light source device according to this exemplary embodiment may further include a reflective plate 370 on the opposite side to the light-receiving face 350 of the two-sided diffusion unit 200. The reflective plate 370 reflects a part of the light coming through the light-receiving face 350 that exits the two-sided diffusion unit 300 back toward the light-receiving face of the two-sided diffusion unit 300. The light reflected back toward the light-receiving face 350 is directed by the diffusion particles 360 toward the front side face 310 and the back side face 320, thereby improving the light utilization efficiency.

A two-sided diffusion unit 400 according to the second exemplary embodiment shown in FIG. 4 includes diffusion particles 460 and a reflective plate 470 on the opposite side to a light-receiving face for improving light utilization efficiency, and the density of the diffusion particles 460 increases away from the light-receiving face, like the two-sided diffusion unit 300 according to the first exemplary embodiment. The two-sided diffusion unit 400 has a wedge-like cross section that widens away from the light-receiving face 450. With such a wedge-like cross section, a front side face 410 and a back side face 420 can be enlarged, and light can exit more evenly.

FIG. 5 is a cross-sectional view of a two-sided, surface light source device according to a third exemplary embodiment of the present disclosure. FIG. 6 is a plan view for illustrating a diffusion pattern by a diffusion unit according to the third exemplary embodiment of the present disclosure.

A two-sided diffusion unit 500 according to the third exemplary embodiment of the present disclosure includes a pair of light guide plates 520 and 540.

As shown in FIG. 5, a first light guide plate 520 is to direct light toward a front side face 522, and a second light guide plate 540 is to direct light toward a rear side face 542.

A light-receiving face 524 of the first light guide plate 520 and a light-receiving face 544 of the second light guide plate 540 are formed in the same plane, and allow the light emitted from the LEDs 120 to be evenly incident on the first light guide plate 520 and the second light guide plate 540.

The first light guide plate 520 and the second light guide plate 540 have inclined faces 525 and 545 opposed to the front side face 522 and the back side face 542, respectively, through which light exits. The diffusion pattern 526 (in FIG. 6) may be formed between the inclined faces. The diffusion pattern 526 may be formed by performing a roughing process to make a rough surface. When light exits out of the light guide plates of a dense medium, the light is reflected off the inclined faces 525 and 545, such that the light exits evenly through the light-exiting faces 522 and 542 of the light guide plates.

Reflective layers 527 and 547 may be further formed on the inclined faces between which the diffusion pattern is formed.

The reflective layers 527 and 547 reflect the light passing through the diffusion pattern to exit the inclined faces back to the light guide plates 520 and 540, thereby improving light utilization efficiency.

As shown in FIG. 6, the area of the diffusion pattern 526 may increase away from the light-receiving face 524. Since the probability that light reaches decreases away from the light-receiving face 524, the diffusion pattern 526 has a trapezoid shape, the area of which increases away from the light-receiving face 524, thereby evenly diffusing the light.

In the above-described exemplary embodiments, the substrate on which the LEDs are disposed as the light source is disposed only on one side of the device. However, a pair of substrates on each of which LEDs are disposed may be disposed facing each other with a two-sided, surface light source device therebetween, as in exemplary embodiments of the present disclosure to be described below.

FIG. 7 is a cross-sectional view of a two-sided, surface light source device according to a fourth exemplary embodiment of the present disclosure.

As shown in FIG. 7, according to the fourth exemplary embodiment, a first substrate 100 and a second substrate 200, on each of which LEDs 120 are disposed, are disposed facing each other with a two-sided diffusion unit 700 therebetween. As a result, light can exit evenly through a front side face 722 and a back side face 742, which are light-exiting faces of the two-sided diffusion unit 700.

The two-sided, surface light source device according to this exemplary embodiment includes the first substrate 100, the second substrate 150, on each of which LEDs are disposed as the light source, and the two-sided diffusion unit 700 that has a plate-like shape with relatively large front side and back side faces. One side face of the two-sided diffusion unit 700 is a first light-receiving face 724 facing the first substrate 100, and the other side face of the two-sided diffusion unit 700 is a second light-receiving face 744 facing the second substrate 150, opposed to the first light-receiving face 724.

The two-sided diffusion unit 700 may include two light guide plates 720 and 740.

The first light guide plate 720 is to diffuse the light received through the first light-receiving face 724 facing the first substrate 100 toward the face 722. The second light guide plate 740 is to diffuse the light received through the second light-receiving face 742 facing the second substrate 150 toward the face 742.

The first light guide plate 720 and the second light guide plate 740 may have a wedge-like shape having inclined faces 725 and 745, respectively, that are the opposing faces to the light-exiting faces 722 and 742, respectively, through which light exits. The inclined faces 725 and 745 of the first light guide plate 720 and the second light guide plate 740, respectively, may face each other.

In addition, reflective layers 727 and 747 may be formed on the inclined faces 725 and 745, respectively, so that leaking light is directed back to the inclined faces, thereby improving light utilization efficiency.

FIG. 8 is a cross-sectional view of a two-sided, surface light source device according to a fifth exemplary embodiment of the present disclosure.

The fifth exemplary embodiment is a modification of the fourth exemplary embodiment of the present disclosure, and includes a two-sided reflective plate 730 between the inclined faces 725 and 745 of wedge-like first and second light guide plates 720 and 740, respectively.

FIG. 9 is a cross-sectional view of a two-sided diffusion unit coupled with LEDs according to an exemplary embodiment of the present disclosure.

A surface light source device according to this exemplary embodiment may include a light source groove 252 surrounding LEDs 120 formed in a light-receiving face 250 of a two-sided diffusion unit 900.

When the LEDs 120 are accommodated in the light source groove 252, the light emitted omnidirectionally from the UV LEDs 120 can be directed into a two-sided diffusion unit 900, thereby improving light utilization efficiency. The feature of the light source groove formed in the light-receiving face of the two-sided diffusion unit 900 may be applied to any of the above-described exemplary embodiments of the present disclosure.

It should be appreciated that the above-described embodiments are illustrative in all aspects but are not limiting. The scope of the present disclosure is defined only by the appended claims rather than the above-mentioned detailed descriptions. In addition, all modifications or alterations deduced from the spirit and the scope of the claims and equivalents thereof are to be construed as falling within the scope of the present disclosure.

The invention claimed is:

1. A two-sided, surface light source device, comprising:
 a substrate;
 light-emitting diodes (LEDs) disposed on the substrate and operable as a light source; and
 a two-sided diffusion unit having a front face, a back face, and a light-receiving face that is perpendicular to the front face and the back face, the light-receiving face facing the substrate, wherein light emitted from the light source is diffused in the two-sided diffusion unit and exits through the front face and the back face, and
 wherein the two-sided diffusion unit comprises diffusion particles and a density of the diffusion particles increases further away from the light-receiving face.

2. The device of claim 1, wherein the two-sided diffusion unit has a cross section that widens away from the light-receiving face.

3. The device of claim 1, wherein the two-sided diffusion unit comprises a first light guide plate diffusing light received through the light-receiving face toward the front face, and a second light guide plate diffusing the light received through the light-receiving face toward the back face.

4. The device of claim 1, wherein the two-sided diffusion unit further comprises a reflective plate on a side face opposed to the light-receiving face.

5. The device of claim 3, wherein the first and second light guide plates have inclined surfaces, and a diffusion pattern is formed between the first and second light guide plates.

6. The device of claim 5, wherein the diffusion pattern is shaped to have an increasing width away from the light-receiving face.

7. The device of claim 3, wherein a reflective layer is formed on each of the first and second light guide plates.

8. The device of claim 1, wherein the two-sided diffusion unit comprises a light source groove in which the LEDs are accommodated.

9. A two-sided, surface light source device using LEDs, the device comprising:
 a first substrate on which LEDs are disposed to operate as a light source;
 a second substrate on which LEDs are disposed to operate as a light source; and
 a two-sided diffusion unit having a first light-receiving face facing the first substrate and a second light-receiving face facing the second substrate, wherein lights emitted from the light sources are diffused in the two-sided diffusion unit and exit through a first face and a second face that are perpendicular to the first light-receiving face and the second light-receiving face, and wherein the two-sided diffusion unit comprises a first light guide plate having a width continuously decreasing along a direction from the first light-receiving face to the second light-receiving face and a second light guide plate having a width continuously increasing along the direction.

10. The device of claim 9, wherein the first light guide plate diffuses light received through the first light-receiving face toward the first face, and the second light guide plate diffuses the light received through the second light-receiving face toward the second face.

11. The device of claim 9, further comprising reflective layers formed on the first light guide plate and the second light guide plate, respectively.

12. The device of claim 9, further comprising a two-sided reflective plate disposed between the first light guide plate and the second light guide plate.

13. The device of claim 9, wherein each of the first and second light guide plates has a light source groove in which the LEDs are accommodated.

14. The device of claim 10, wherein the first light guide plate and the second light guide plate have inclined surfaces.

15. The device of claim 10, wherein the two-sided diffusion unit includes one of a polymethyl methacrylate (PMMA), an acryl polymer containing methyl methacrylate (MMA) monomers of 85 weight % to 100 weight %, and quartz.

16. The device of claim 10, wherein the two-sided diffusion unit has a plate shape.

17. The device of claim 1, wherein the two-sided diffusion unit has a plate shape.

18. The device of claim 1, wherein the two-sided diffusion unit includes one of a polymethyl methacrylate (PMMA), an acryl polymer containing methyl methacrylate (MMA) monomers of 85 weight % to 100 weight %, and quartz.

* * * * *